United States Patent
Graf et al.

(10) Patent No.: US 8,852,508 B2
(45) Date of Patent: Oct. 7, 2014

(54) MICROINJECTION APPARATUS AND METHOD

(75) Inventors: Siegfried Graf, Luzern (CH); Helmut Knapp, Ebikon (CH)

(73) Assignee: CSEM Centre Suisse d'Electronique et de Microtechnique SA—Recherche et Developpement, Neuchatel (CH)

( * ) Notice: Subject to any disclaimer, the term of this patent is extended or adjusted under 35 U.S.C. 154(b) by 283 days.

(21) Appl. No.: 12/864,349

(22) PCT Filed: Jan. 22, 2009

(86) PCT No.: PCT/EP2009/050710
§ 371 (c)(1),
(2), (4) Date: Jul. 29, 2010

(87) PCT Pub. No.: WO2009/092759
PCT Pub. Date: Jul. 30, 2009

(65) Prior Publication Data
US 2011/0003326 A1   Jan. 6, 2011

Related U.S. Application Data

(60) Provisional application No. 61/006,603, filed on Jan. 23, 2008.

(51) Int. Cl.
| | | |
|---|---|---|
| G01N 33/483 | (2006.01) | |
| C12N 15/00 | (2006.01) | |
| G01N 21/00 | (2006.01) | |
| C12M 1/00 | (2006.01) | |
| C12M 1/42 | (2006.01) | |

(52) U.S. Cl.
CPC ............... C12M 23/50 (2013.01); C12M 35/00 (2013.01)

USPC .......... 422/64; 422/63; 422/82.07; 435/285.1; 435/288.7

(58) Field of Classification Search
USPC ............ 422/63–67, 82.05–82.11; 436/46–48, 436/63; 435/455–490, 285.1–285.3, 286.2, 435/286.6, 288.7
See application file for complete search history.

(56) References Cited

U.S. PATENT DOCUMENTS 4,186,187 A * 1/1980 Jahnsen et al. ................... 422/64
5,231,029 A * 7/1993 Wootton et al. ............ 435/303.2
(Continued)

OTHER PUBLICATIONS

Multi Channel Systems, Automated injection, [online], [initially visited on Jan. 19, 2009], Retrieved from the website <URL: http://www.multichannelsystems.com/products-mea/xenopus-laevis-research/automated-injection.html>.

(Continued)

*Primary Examiner* — Jan Ludlow
(74) *Attorney, Agent, or Firm* — Preti Flaherty Beliveau & Pachios LLP

(57) ABSTRACT

The present invention discloses a microinjection apparatus (100) for microinjection of substances into individual substances comprising at least one carrier (120, 130) on which at least one sample is immobilizable. In embodiments, the apparatus comprises at drivable support (110) on which at least one carrier is positioned, wherein the support drives the at least one carrier in a closed loop to a respective plurality of stations along the loop. The plurality of stations constitutes at least one sample-substance-providing station (141), at least one sample-substance microinjection station (142) and at least one sample-extraction station (143).

9 Claims, 7 Drawing Sheets

(56) References Cited

U.S. PATENT DOCUMENTS

| | | | |
|---|---|---|---|
| 6,593,129 B1 * | 7/2003 | Takeshita et al. | 435/285.1 |
| 7,914,739 B2 * | 3/2011 | Heiner et al. | 422/64 |
| 2006/0024812 A1 * | 2/2006 | Youoku et al. | 435/285.1 |
| 2006/0104862 A1 * | 5/2006 | Pages Pinyol | 422/64 |
| 2006/0246571 A1 * | 11/2006 | Youoku et al. | 435/285.1 |
| 2007/0059818 A1 * | 3/2007 | Yabuki et al. | 435/288.4 |
| 2011/0038836 A1 * | 2/2011 | Cooper et al. | 424/93.2 |

OTHER PUBLICATIONS

Multi Channel Systems, MCS GmbH, Reutlingen, Germany, "roboocyte User Manual," [online], [retrieved Jan. 19, 2009], retrieved from the website <URL: http://www.multichannelsystems.com/fileadmin/user_upload/Manuals/Roboocyte_Manual_ClampAmp2.pdf>.

Fujitsu Laboratories Ltd., Automated Microinjection Technology, [online], [initially visited on Jan. 19, 2009], retrieved from the website <URL: http://jp.fujitsu.com/group/labs/downloads/en/business/activities/activities-3/fujitsu-labs-bio-002-en.pdf>.

J. N. Dumont "Oogenesis in Xenopus laevis (Daudin). I. Stages of oocyte development in laboratory maintained animals". J. Morphol. vol. 136, Issue 2, 153-179, Feb. 1972.

* cited by examiner

MICROINJECTION APPARATUS AND METHOD

FIELD OF THE INVENTION

Generally, the present invention refers to the field of drug screening, and in particular to the microinjection of substances into cell-based samples for performing such screening.

BACKGROUND OF THE INVENTION

Cell-based samples may become for some applications the preferred choice of screening in drug discovery research, potentially overtaking more traditional approaches that include animal models. The samples may be used to detect specific cellular pathways of chemical compounds, therapeutic proteins, synthetic ribonucleic acid (siRNA) agents and other structures of interest. Insights from these samples could enable more efficient discovery of effective drugs compared to non-cell-based samples, thus saving time and costs as well as the need for future secondary screens.

Cell-based samples may be used during the early phase of the drug discovery process such as for cell-based ion channel expression systems (e.g. hERG k+) in association with automated patch clamp assays. Using cell-based samples enables high throughput safety testing, such as cardiotoxicity or hepatoxicity of chemicals. For example, the introduction of desoxyribonucleic acid (DNA), siRNA, or other substances into cells is a micromanipulation technology applied to develop and optimize various cellular systems, which enables cell systems either to more closely approximate in vivo testing or to become more competent or more specific for various in vitro applications.

Methods for microinjecting (e.g., transfecting) substances into cell-based samples such as for example, DNA, siRNA or monoclonal antibodies (mAbs) may be divided into three categories: a) chemical carriers; b) Viral vectors used by biologists to deliver genetic material inside a living cell by infection, and c) physical procedures that introduce material directly into the cells. All those three methods have advantages and disadvantages depending on the type of application.

Chemical carriers generally comprise positively-charged liposomes that are specialized in transfecting different cell types. However, chemical carriers have a relatively high transfection success only in certain cell types. In addition, liposomes can cause cytotoxicity and may induce a potent unexpected cell response. These limitations for chemical carriers prevent analysis of more biologically-relevant cell types, and also can significantly affect experimental outcomes and drastically interfere with the understanding of a gene's function.

Viral vectors' asset lies in their ability to achieve a very high percentage of successful transfection. However, to successfully perform transfection, excellent operator skills are required. In addition, the operator may have to undertake distinctive safety measures. Viral vectors also have the drawback of unwanted influences on the cell-based samples and that the size of injectable DNA is limited. In any case, working with infectious or potentially infectious particles, coupled with the possibility of raising undesirable immune response from an organism, counterbalances the high transfection rates, especially for the clinical research.

Physical procedures of transfection may again be subdivided into three different categories. A first category refers to Electroporation systems, which uses electrical pulses to open up the membranes of mammalian cells for the passage of genes. A second category refers to microinjection, and a third category refers to Gene gun devices. Gene gun devices insert samples of DNA or RNA more directly and ensure more localized delivery. However, employing physical procedures may cause a relatively low viability of cell-based samples. Electroporation for example may kill about 50% of the cell based samples.

Substances may also be inserted into cell-based samples using manual or semi-automated microinjection procedures, which are ways of introducing DNA and various compounds for new drugs only into the type of cells that are adherent in culture. Generally, microinjection allows the introduction of molecules into a defined cell population at a known concentration, whilst the timing of the experiment is stringently controllable; several types of reagents may be simultaneously introduced into cells (e.g., DNA constructs may be co-injected with a labelled dextran to mark the injected cells); reagents may be introduced such as, for example, antibodies, peptides, siRNAs, dyes, and chemical substances, whilst generally maintaining the viability of the cells. Microinjection procedures require searching for a cell under the microscope, catching the cell with a patch-clamp-like pipette, positioning the micropipette, puncturing the cell with a glass hollow-needle (apex only few microns) and injecting the liquid containing the transfection material into the cell. Performing these steps manually may take up to 10-15 min per cell. Therefore, performing these steps using manual or semi-automated procedures for may be tedious and time-consuming. In addition, only a limited number of cells may be involved, which may not permit the subsequent analysis of effects upon some biochemical parameters. The major limitation of the approach is the small amount of microinjected cellular material obtained. Therefore, performing microinjection as known in the art can not be used in association with cell-based high throughput screening (HTS).

A semiautomatic microinjection apparatuses is disclosed in the following URLs by "Multi Channel Systems": http://www.multichannelsystems.com/products-ion.html, and http://www.multichannelsystems.com/fileadmin/user_upload/Manuals/Roboocyte_Manual_ClampAmp2.pdf, both of which were visited on Jan. 19, 2009. Fujitsu discloses a microinjection apparatus in the following URL http://www-.computers.us.fujitsu.com/www/products_bioscience.shtml?products/bioscience/cellinjector, which was visited on Jan. 18, 2009.

BRIEF DESCRIPTION OF THE FIGURES

Features of the invention will become more clearly understood in the light of the ensuing description of a some embodiments thereof, given by way of example only, with reference to the accompanying figures, wherein.

DESCRIPTION OF THE EMBODIMENTS OF THE INVENTION

It is an object of the invention to overcome the above-mentioned drawbacks associated with manual or semiautomated microinjection by introducing an automated microinjection method and apparatus. The automated microinjection method and apparatus according to an embodiment of the invention may, for example, enable high throughput screening (HTS).

It should be understood that where the claims or specification refer to "a" or "an" feature, such reference is not to be construed as there being only one of that element. Accordingly, "an" or "a" feature may also encompass the meaning of "at least one" of the feature. For example, "a carrier" and "a sample" may also include the meaning of "at least one carrier" and "at least one sample", respectively.

Figure 1:
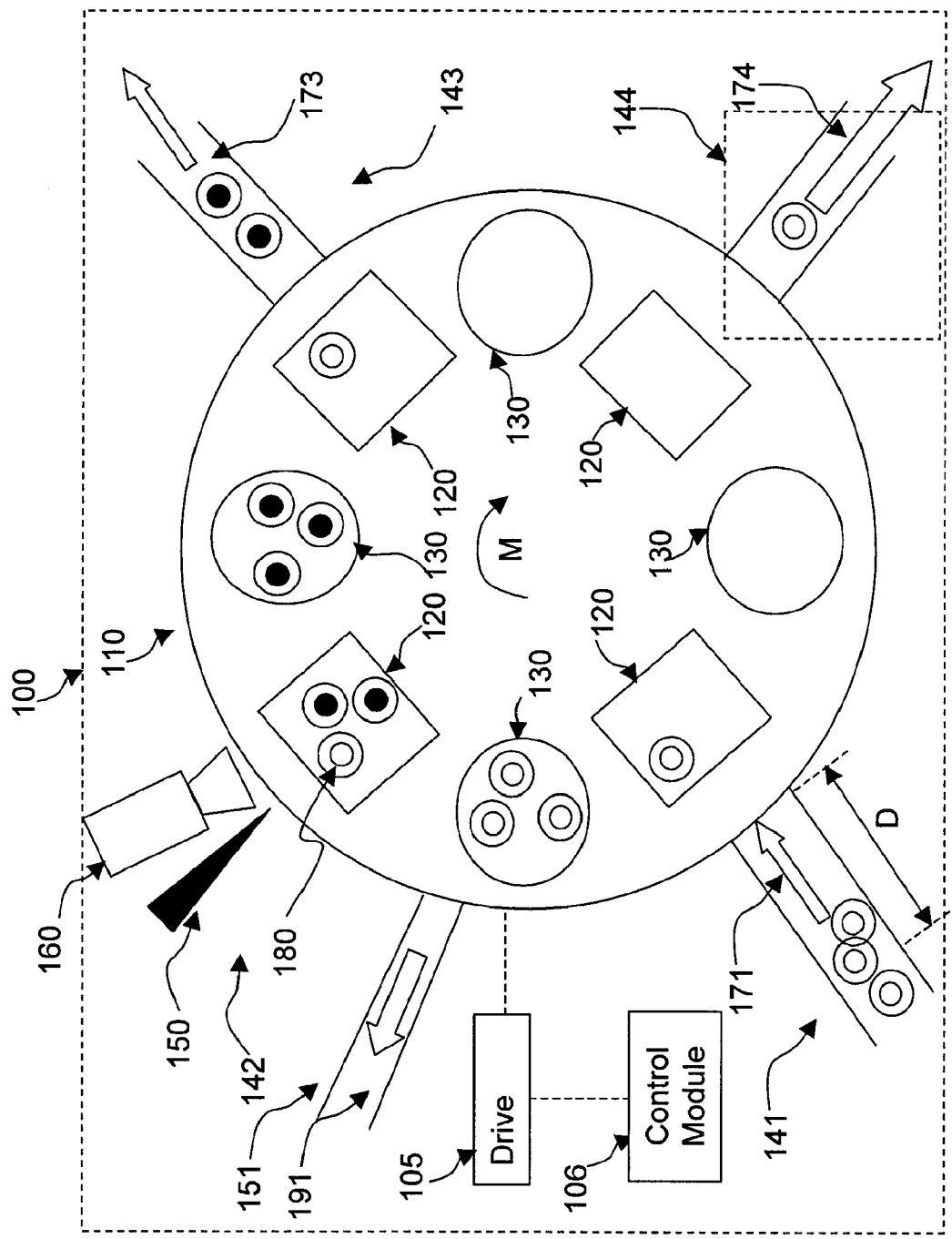
FIG. 1 is a schematic top view illustration of an automated microinjection apparatus, according to an embodiment of the invention.

Reference is now made to FIG. 1. According to some embodiments of the invention, a first automated microinjection apparatus 100 enabling microinjection into individual samples such as, for example, hard-to-transfect cells includes a drivable support 110 that is operatively coupled with a drive 105, a control module 106 and a power supply (not shown). Support 110 may include a carrier such as for example at least one first carrier 120 and/or at least one second carrier 130. For exemplary purposes and to simplify the discussion that follows, embodiments of the present invention may hereinafter be outlined with reference to first carrier(s) 120 only (hereinafter "carrier"). Carrier(s) 120 may be detachably coupleable to support 110 and may be adapted to enable immobilizing thereon at least one individual sample 180 embodied, for example, by a cell. Drive 105 causes first carrier 120 to drive in a stepwise and/or continuous manner in a closed loop to a plurality of stations at respective positions along said loop. The plurality of stations may include at a first position a sample-providing station 141, which may be equipped with a pressure line and a sample-supply line 171; at a second position a microinjection station 142; at a third position a sample-extraction station 143 comprising a sample-extraction line 173; and optionally at a fourth position a sample-removal station 144 comprising a sample-extraction line 174.

According to some embodiments of the invention, both successfully and unsuccessfully microinjected sample(s) 180 may be removed from sample-extraction station 143. Removed sample(s) 180 may then be sorted, either manually or automatically for successfully and unsuccessfully microinjected sample(s) 180. In some embodiments, sample-extraction station 143 may be adapted to control sample(s) 180 for the success of the performed microinjection. Sample-extraction station 143 may be adapted to remove successfully microinjected sample(s) 180 from carrier(s) 120 and correspondingly, sample-removal station 144 may be adapted to remove unsuccessfully microinjected sample(s) 120. Alternatively, sample-extraction station 143 may be adapted to remove unsuccessfully microinjected sample(s) 180 from carrier(s) 120. Accordingly, sample-removal station 144 may be adapted to remove successfully microinjected sample(s) 180 from carrier(s) 120.

According to some embodiments, the plurality of stations may further include a sample-extraction station 151 between sample-providing station 141 and microinjection station 142, wherein sample-extraction station 151 may comprise a sample-extraction line 191. Non-usable sample(s) 180 may be removed at sample-extraction station 151, whereas usable sample(s) 180 may be further conveyed to microinjection station 142.

In some embodiments, sample-providing station 141 and/or sample-extraction station 151 may be adapted to control sample(s) 180 for their usability to be microinjected. Additionally or alternatively, microinjection apparatus 100 may be adapted control sample(s) 180 for their usability between sample-providing station 141 and sample-extraction station 151 and/or prior to sample-providing station 141.

Sample-extraction station 143 and/or sample-removal station 144 and/or first sample-extraction station 151 may be equipped with a pressurizing device (not shown) comprising a pressure line (not shown), which when operational, may facilitate or enable the removal of sample(s) 180.

According to some embodiments of the invention, a microinjection device such as, for example, microinjection apparatus 100 may include an inactive stopover location between two stations (e.g., between sample-providing station 141 and microinjection station 142) at which support 110 may be stopped whilst simultaneously at other position(s) the respective station(s) may be or become active.

Initially, carrier 120 may be positioned at sample-providing station 141, whereupon for example at least one individual sample 180 may be provided onto carrier 120 via sample-supply line 171. Sample-supply line 171 may be adapted to provide sample(s) 180 by gravitation, i.e., sample(s) 180 may simply fall due to gravitation through sample-supply line 171 onto or into carrier(s) 120. In some embodiments, sample-supply line 171 of sample-providing station 141 may have a length D of, e.g., at least 10 cm, allowing sample(s) 180 to be guided by gravitation into an orientation suitable for performing microinjection. If sample(s) 180 is/are for example embodied by Xenopus Oocytes, the animal pole thereof has to be faced up relative to carrier(s) 120 to facilitate microinjection at microinjection station 142. Since vegetal pole of Xenopus Oocytes is generally denser than the animal pole, the length D of sample-supply line 171 may allow gravitational force to adjust the orientation of Xenopus Oocytes such that the animal pole is faced upwardly when engaging with carrier(s) 120.

Subsequently, sample(s) 180 may be immobilized, e.g., by subjecting them to negative pressure (which may be negative relative to the surrounding pressure), and optionally conveyed to sample-extraction station 151 that is adapted to identify usable and/or non-usable sample(s) 180 using, for example, an optical control (not shown). In accordance with the identification of the usable and/or non-usable sample(s) 180, non-usable sample(s) 180 may be removed from first carrier 120. Non-usable sample(s) 180 may for example be characterized by being mobilized, too small and/or disoriented, and the like, such that sample(s) 180 is/are non-injectable. According to some embodiments of the invention, carrier 120 may be driven from sample-providing station 141 directly to microinjection station 142.

Microinjection station 142 may be equipped with an injection device 150 operatively coupled with an optical control 160. Optical control 160 may be adapted to identify the position and optionally the orientation of each of usable sample(s) 180. Penetrating the needle of injection device 150 into sample(s) 180 may be performed in accordance with at least one of the following techniques: visual feedback, force-feedback and by defining a nominal penetration depth. For example, injection device 150 may be provided with information related to the position and/or orientation of sample(s) 180. In response, force-feedback injection device 150 may position the tip of its needle into respective sample(s) 180, whilst the needle's penetration depth into sample(s) 180 may be performed in accordance with the force required to penetrate sample(s) 180. Upon penetration a substance may be microinjected into at least some of sample(s) 180, and the needle may then be retracted from sample(s) 180. Carrier(s) 120 may then be positioned at sample-extraction station 143, where either one or both successfully or unsuccessfully microinjected sample(s) 180 are removed from carrier(s) 120, for example, in accordance with information received from a visual control (not shown). Optionally, microinjection apparatus 100 may further include sample-removal station 144, which may be adapted to extract or remove successfully or unsuccessfully microinjected sample(s) 180, in correspondence with sample(s) 180 removed from sample-extraction station 143.

According to some embodiments of the invention, support 110 may be embodied by a turntable, by an endless conveyor belt, or by any other suitable sample-conveying device.

It should be noted that embodiments of support 110 may be manufactured such that at least some of the components thereof may be sterilizable, e.g., by an autoclave. If some of the components are non-sterilizable, they may be replaceable and disposable.

Figure 2:
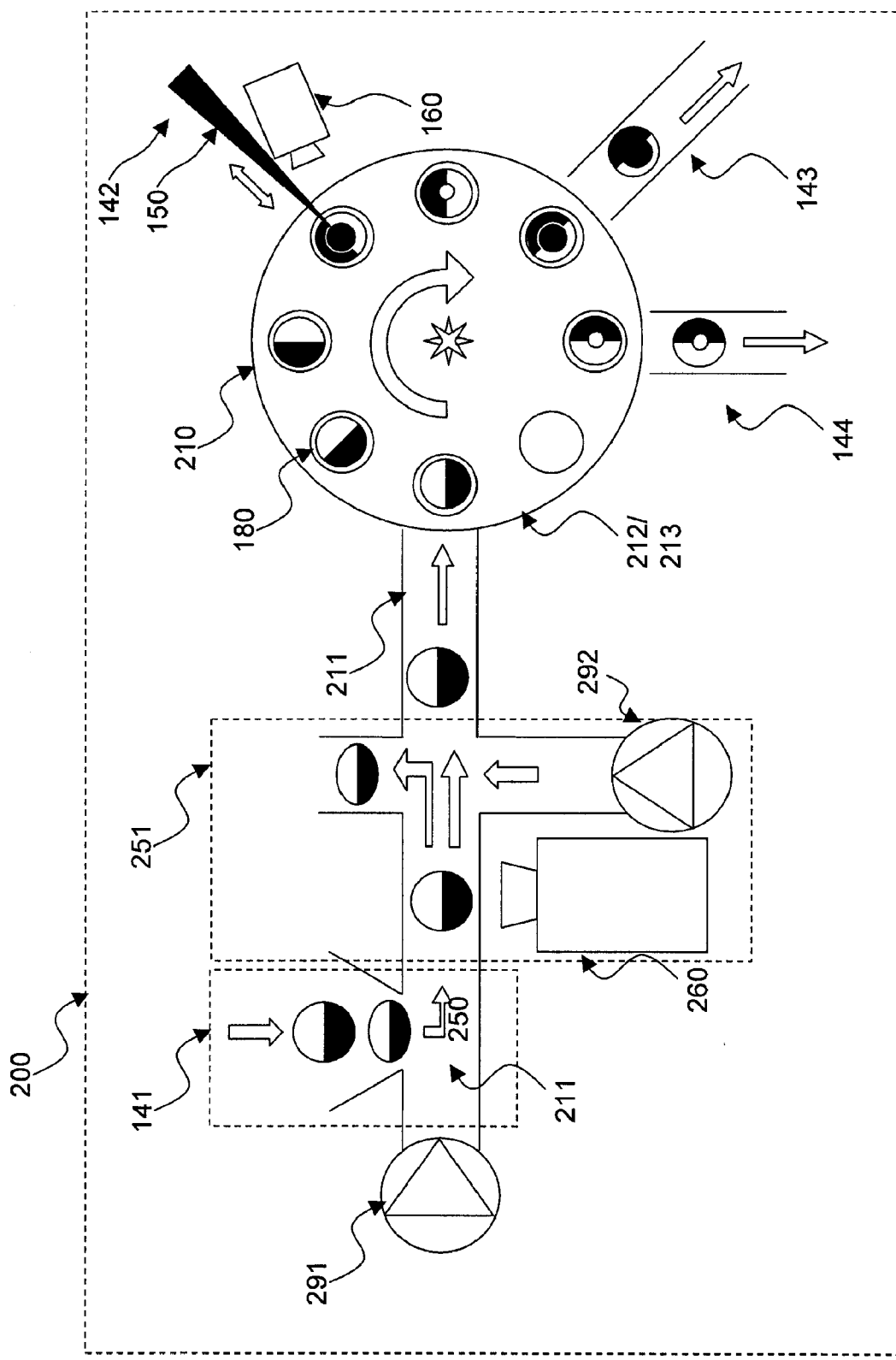
FIG. 2 is a schematic top view illustration of an automated microinjection apparatus, according to another embodiment of the invention.

Reference is now made to FIG. 2. According to some embodiments of the invention, a second microinjection apparatus 200, which may be employed for the microinjection of, e.g., big dissociated cells, may in principle be similarly configured to first microinjection apparatus 100, except for that a support 210 of microinjection apparatus 200 may be embodied in a first part by a channel 211 and in a second part either by a turntable 212 or a conveyer belt 213. Additional control may also be employable as outlined hereinafter.

Channel 211 may be operatively coupled with a drive pump 291 such that sample-conveying fluid may be driven in channel 211 causing sample(s) 180 provided at sample-providing station 141 to be conveyed as is schematically illustrated with arrow 250. Second microinjection apparatus 200 may employ an optical control 260 along channel 211 for determining which of samples 180 are suitable for microinjection and which not in accordance with at least one criterion such as, for example, position, orientation, colour, contrast and size of sample(s) 180. In correspondence with optical control 260, non-usable samples 180 may be removed from second sample-extraction station 251, for example, by operating a waste pump 292. Usable samples 180 may then be flown by drive pump 291 to turntable 212 or conveyor belt 213 for further transportation of samples 180 sequentially to microinjection station 142, to sample-extraction station 143 and to sample-removal station 144, as outlined hereinabove with reference to FIG. 1. According to some embodiments of the invention, a plurality of optical controls 260 (not shown) may be employed for additional verification of the at least one criterion concerning the suitability of sample(s) 180 to be subjected to microinjection.

Figure 3:
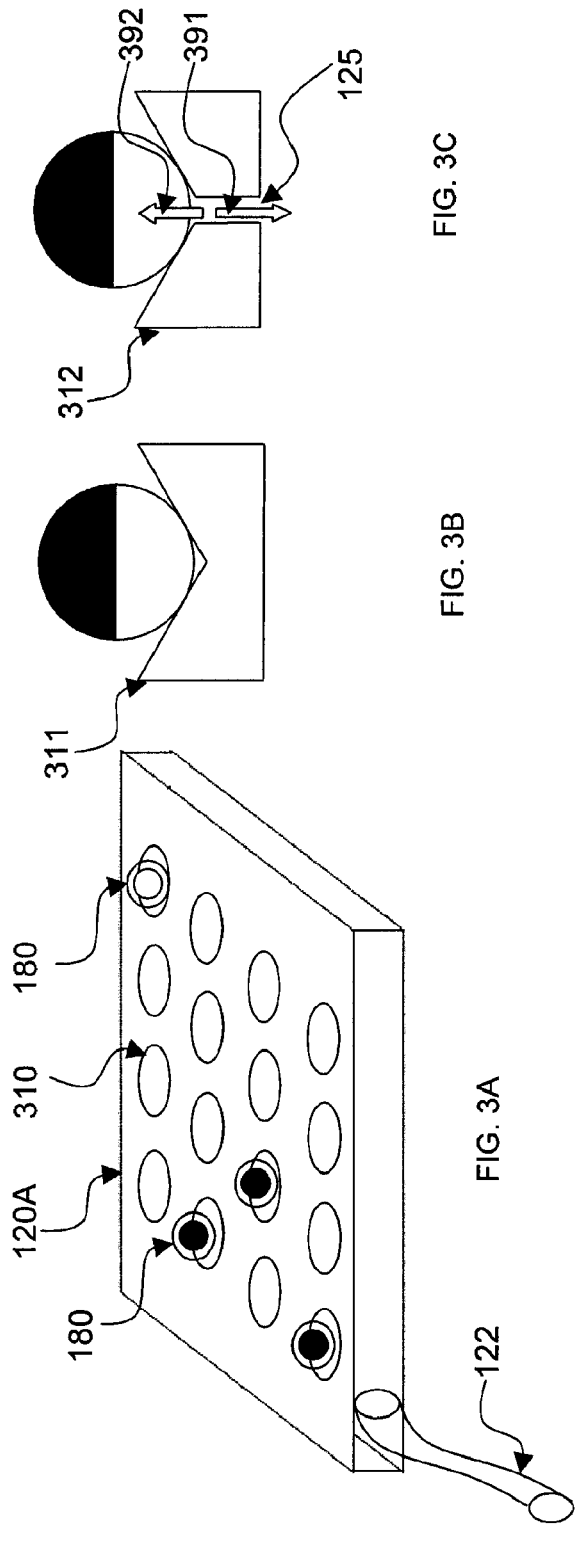
FIG. 3A is a schematic isometric view illustration of a carrier, according to an embodiment of the invention.
FIG. 3B is a schematic side view illustration of an immobilization site, according to an embodiment of the invention.
FIG. 3C is a schematic side view illustration of an immobilization site according to another embodiment of the invention.
FIG. 3D is a schematic isometric illustration of a carrier, according to another embodiment of the invention.
FIG. 3E is a schematic isometric illustration of an immobilization site, according to a yet other embodiment of the invention.

Reference is now made to FIG. 3A, which schematically illustrates an embodiment of carrier(s) 120 (hereinafter referred to as "first carrier 120A"). Carrier 120A may include immobilization recesses 310 adapted to immobilize thereon respective samples 180. Embodiments of immobilization recesses 310 are schematically illustrated in FIG. 3B and FIG. 3C. FIG. 3B for example schematically illustrates an immobilization site 311 having e.g., a recess that is, for example, conically shaped. Thusly configured, the planar movement of, e.g., sample(s) 180 is confined. Additionally, as is schematically illustrated in FIG. 3C, an immobilization site 312 may comprise a pressure line 125 that operatively communicates with a pressure pump (not shown) via a corresponding pressure pipe 122 for generating either negative or positive pressure within immobilization site 312. By generating negative pressure (relative to the surrounding pressure), sample(s) 180 is subjected to negative pressure-based force sucking sample(s) 180 into immobilization site 312, as is schematically illustrated with arrow 391. Alternatively, pressure pump and pressure line 125 may be adapted to subject sample(s) 180 to positive pressure for facilitating the extraction or removal of sample(s) 180, e.g., at sample-extraction station 143 and/or sample-removal station 144, as is schematically illustrated with arrow 392.

Reference is now made to FIG. 3D and FIG. 3E. FIG. 3D schematically illustrates another embodiment of carrier 120 (hereinafter referred to as first carrier 120B). First carrier 120B may include an immobilization site 313 having a modified surface 314 and optionally a recess of, e.g., conical shape. Modified surface 314 may be adapted to enable chemistry-based immobilization such that by subjecting surface 314 with an electrical field and/or specific temperature(s) the wettability of surface 314 may be altered, thereby optionally enabling immobilization of sample(s) 180.

It should be noted that the recesses as schematically illustrated in FIG. 3B, FIG. 3C and FIG. 3E are of conical shape for exemplary purposes only, and that recesses 310 may have any other suitable shape (e.g., spherical). It should further be noted that in some embodiments, modified surface 314 may also be employed in association with suction channel 125. According to some embodiments, first carrier 120 may be recess-free, but may have modified surface 314 and/or be in operative communication with suction channel 125.

It should be noted that in some embodiments of the invention, negative-pressure may be applied above sample-extraction station 143 and/or sample-removal station 144 and/or sample-extraction station 151 to facilitate the removal of sample(s) 180. In some embodiments, sample-providing station 141 may be configured with a buffer flux (not shown) to facilitate the positioning of sample(s) 180. The term buffer flux as used herein refers to carrier liquid of a sample, which may flow continuously, in contrast to a liquid aliquot containing sample 180.

Figure 4:
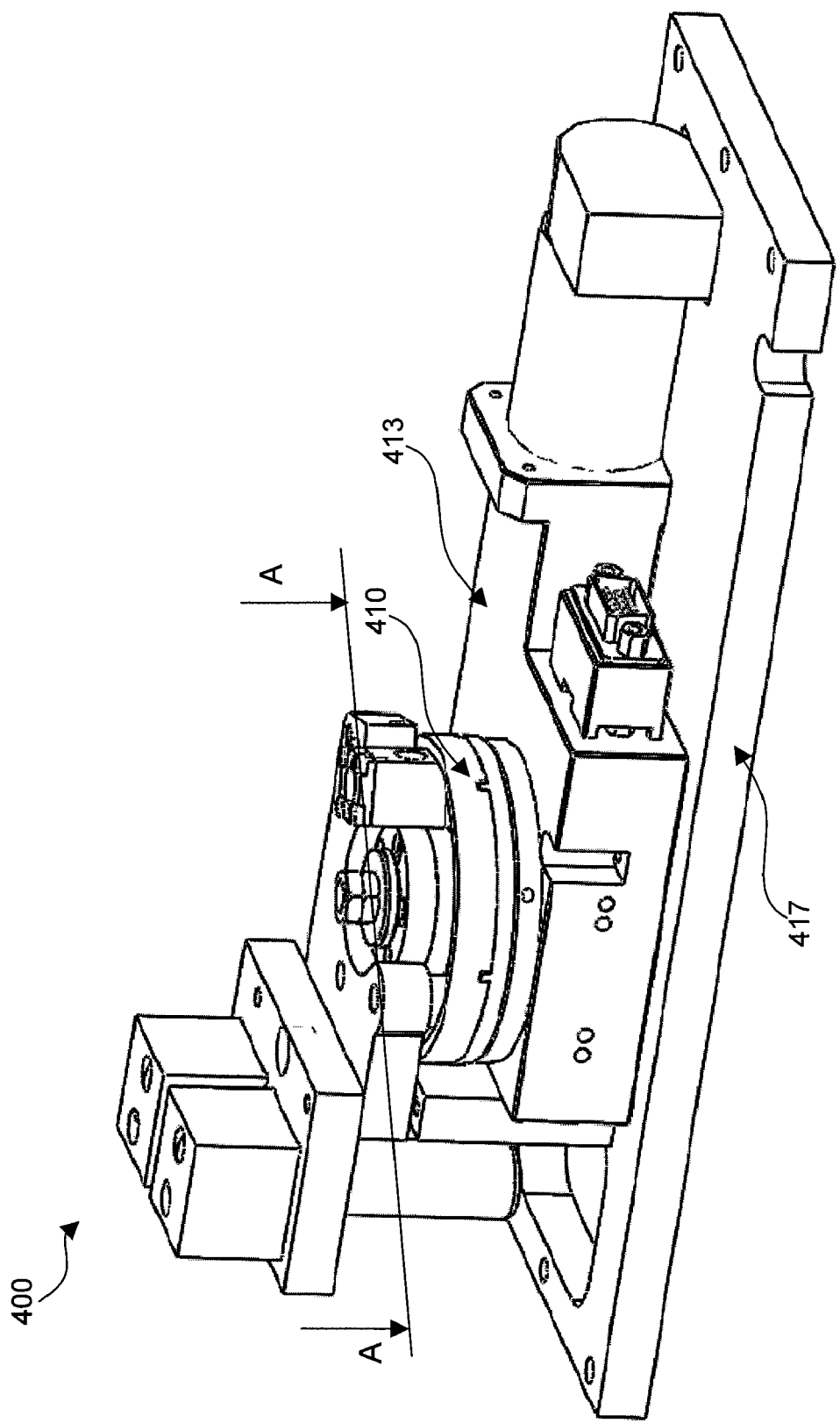
FIG. 4 is a schematic isometric assembly view illustration of a microinjection apparatus, according to an alternative embodiment of the invention.
Figure 5:
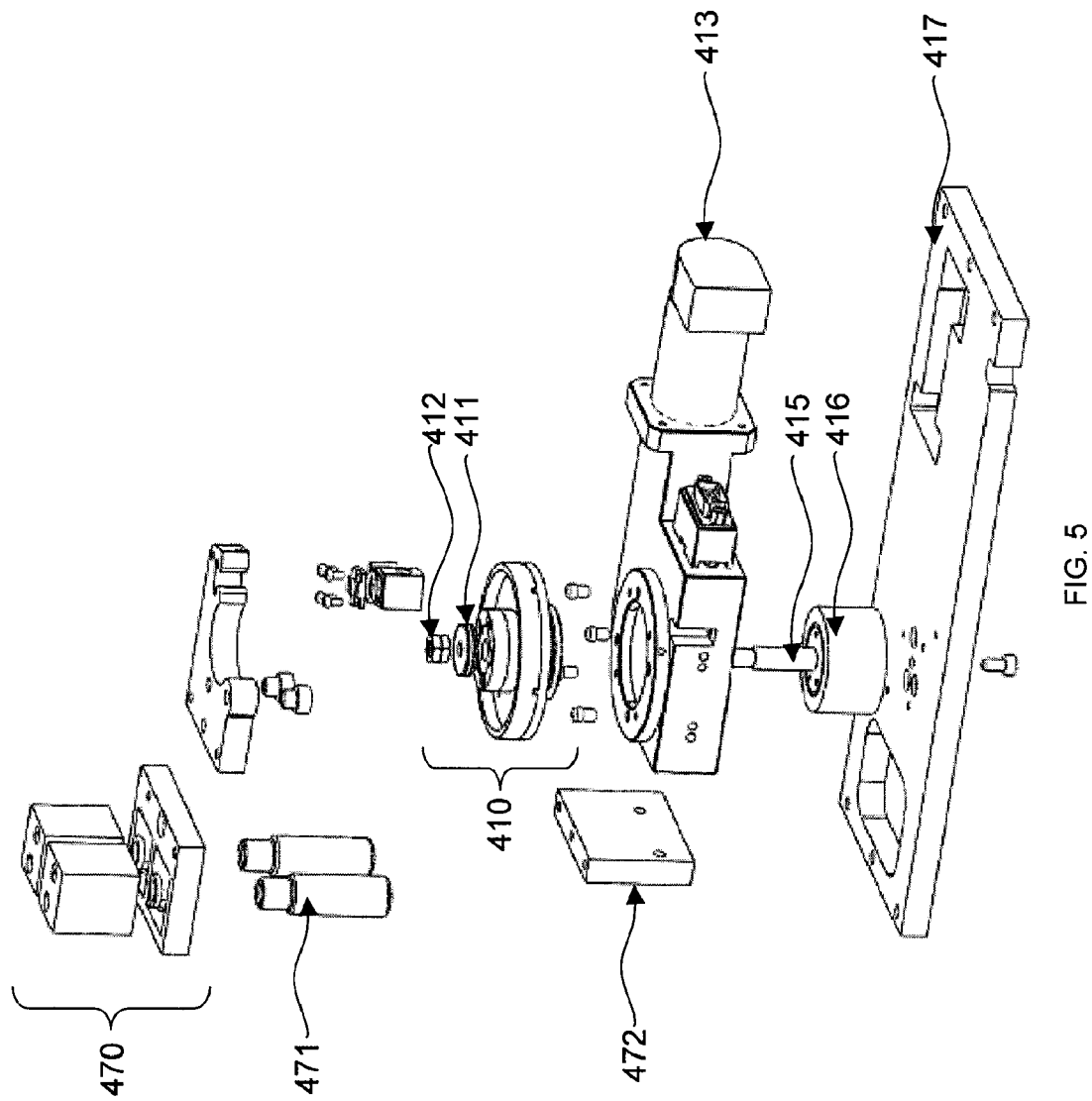
FIG. 5 is a schematic isometric exploded view illustrate of the microinjection apparatus of FIG. 4.

Reference is now made to FIG. 4 and to FIG. 5. A microinjection apparatus 400, which may be an embodiment of microinjection apparatus 100, may include a drivable support 410, which may comprise a bearing 411 (e.g., a needle bearing), fasteners 412 (e.g., screw nuts) for fastening drivable support 410 on a rotation stage 413. Drivable support 410 further includes a shaft 415 for turning support 410, whereby shaft 415 may be rotatably coupled with an endport 416 to a baseplate 417. Endport 416 may be fixedly coupled with endport fasteners 418 to baseplate 417.

Microinjection apparatus 400 may further employ a receptacle holder 470 for holding receptacles 471, wherein receptacle holder 470 may be supported by a holder support 472 for the operative communication with support 410.

Figure 6:
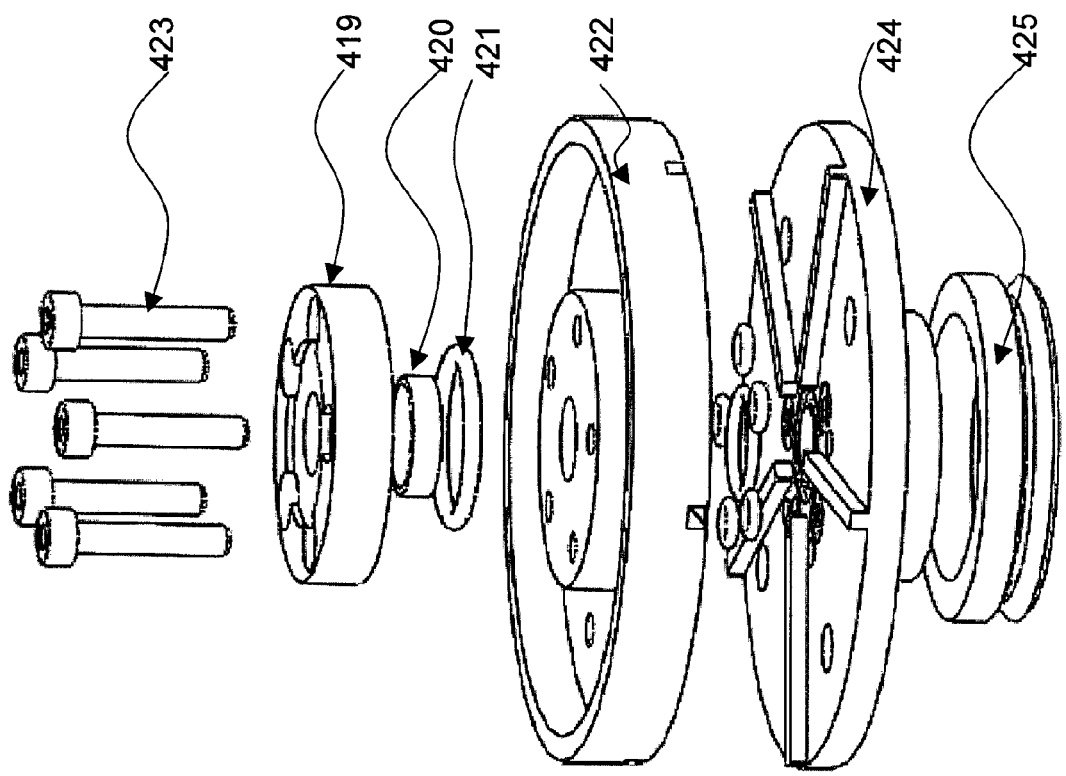
FIG. 6 is a schematic isometric exploded view of a support, according to the embodiment of the FIG. 4.

Additional reference is now made to FIG. 6. According to some embodiments of the invention, support 410 may further include a seal holder 419 for holding rotary seal 420 and O-ring 421, whereby seal holder 419 may be fixedly positioned onto a dish 422 by seal fastener 423, which may be embodied, for example, by screws. Support 410 may further include a middle port 424 that is slidably positioned for rotation on a port O-ring 425.

Figure 7:
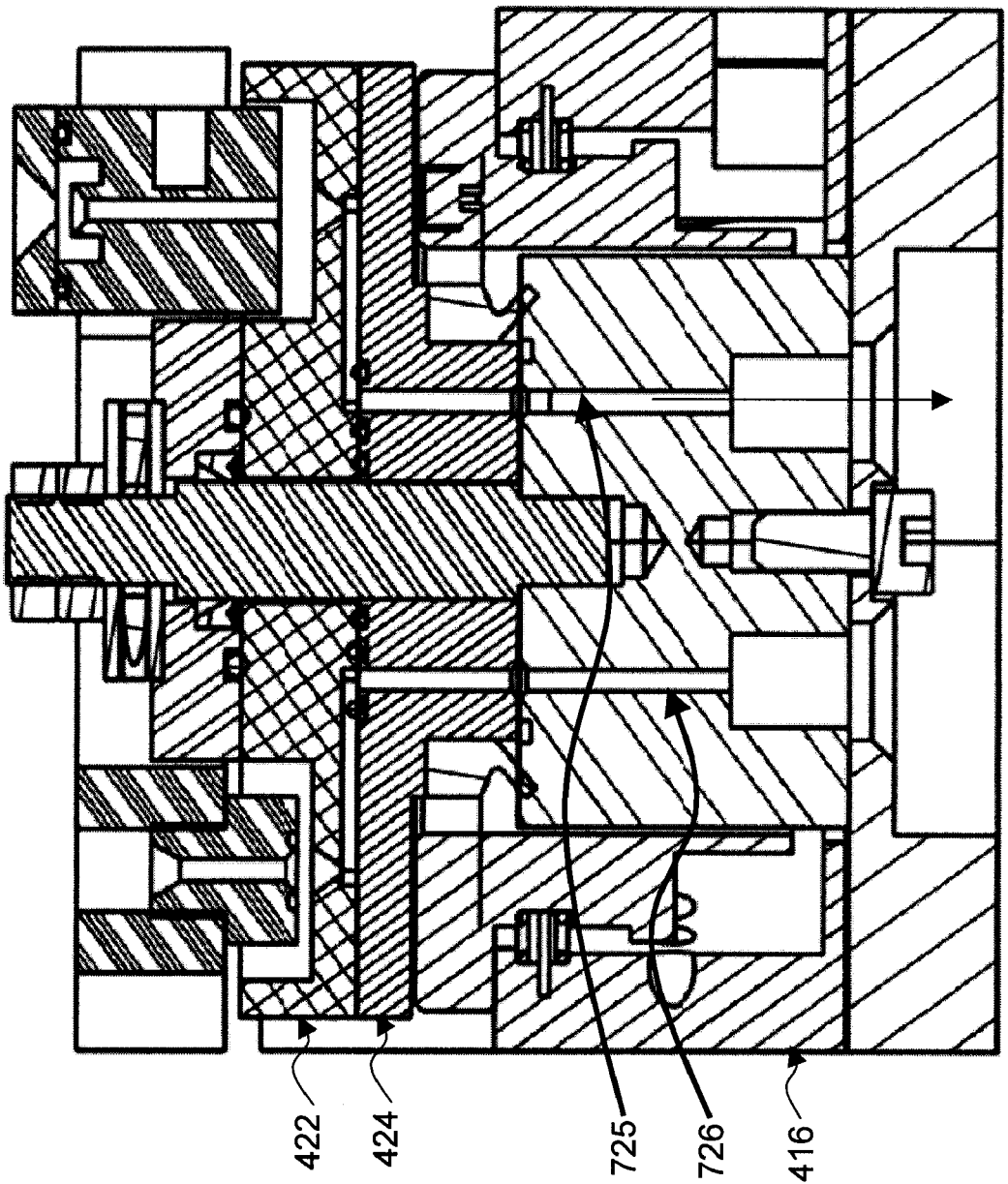
FIG. 7 is a partial cross-sectional side view illustration according to line A-A the microinjection device according to the embodiment of FIG. 4.

Reference is now made to FIG. 7. Endport 416, which may be static, as well as middle port 424 and dish 422, both of which may be rotatable by a drive (not shown), may comprise at least one negative-pressure line 725 as well as at least one positive-pressure line 726. Negative-pressure line(s) 725 of middle port 424 and of dish 422 may be stepwise positionable such to be in alignment with negative-pressure line(s) 725 and pressure line(s) 726 of endport 416 at respective stations. Sample-providing station 141 for example may be embodied as is schematically illustrated in FIG. 7 and thus be configured with negative-pressure line(s) 725 for immobilizing sample(s) 180. Similarly, sample-extraction station 143 and/or sample-removal station 144 and/or sample-extraction station 151 may be equipped with pressure line(s) 726 of a pressurizing device (not shown) enabling the removal of sample(s) 180.

According to some embodiments of the invention, pressure line 726 may be operatively coupled with a receptacle (not shown) for the storage of one or more of samples 180.

A method for performing automated microinjection of sample(s) 180 that are adjusted, immobilized, examined and injected on and then conveyed by a selected one of carrier(s) 120 is outlined hereinafter.

It should be noted that in embodiments of the invention, at least two of the method steps outlined herein may be performed concurrently at respective positions and thus at respective stations.

The method may include providing carrier(s) 120 at sample-providing station 141 with sample(s) 180 from sample-supply line 171. The method may further include immobilizing sample(s) 180 at sample-providing station 141, e.g., by engaging negative-pressure line 125, by gravitation, form and surface modification or any combination thereof.

The method may then include conveying carrier(s) 120 to microinjection station 142, wherein microinjection is performed. Microinjection may for example, be performed by employing optical control 160 which may control for the position of the microinjection device (e.g., a glass needle). The optical control may be performed, e.g., as known in the art, using an automatic or manual vision feedback. Correspondingly, immobilized sample(s) 180 may be in direct line-of-sight with the needle of injection device 150.

According to some embodiments of the invention, the penetration depth of the needle of injection device 150 can either be nominally set or can additionally or alternatively be controlled by a force- and/or vision-feedback. Microinjection may be performed manually or automatically. The method may further include moving forward and backward the needle according to an adjustable injection movement.

Subsequently, the method may include conveying carrier(s) 120 to sample-extraction station 143, where either one or both successfully or unsuccessfully microinjected sample(s) 180 may be discharged from carrier(s) 120 via sample extraction-line 173. If only successfully microinjected samples 180 are discharged from carrier(s) 120 at sample-extraction station 143, the method may further include conveying carrier(s) 120 to sample-removal station 144, where the remaining unsuccessfully microinjected samples 180 are removed. Alternatively, if only unsuccessfully microinjected samples 180 are extracted from carrier(s) 120 at sample-extraction station 143, the method may include conveying carrier(s) to sample-removal station 144, where successfully microinjected samples 180 may be removed. In order to remove either successfully or unsuccessfully samples from sample-extraction station 143, the method may include controlling sample(s) 180 (e.g., by employing a visual control) after microinjection station 142 for the success of the performed microinjection. The control for the success of the performed microinjection may be done at any stage after finalization of the microinjection and may thus be performed, for example, at microinjection station 142 and/or between microinjection station 142 and sample-extraction station 143 and/or at sample-extraction station 143 and/or after sample extraction station 143.

Generally speaking, the method includes conveying carrier(s) 120 in a closed loop from a given position to a subsequent position whilst maintaining the immobilization of at least one usable sample(s) 180. Therefore, the method may include conveying carrier(s) from sample-removal station 144 to sample-providing station 141, since the given position of, e.g., carrier(s) 120 may be a final position that corresponds to sample-removal station 144, and the subsequent position of carrier(s) 120 may thus be the first position corresponding to sample-providing station 141.

It should be noted that the method may be applied in some embodiments in association with large dissociated samples and may thus include providing each immobilization site of, e.g., carrier(s) 120 with a respective single sample 180. Accordingly, the method may include performing between the first and the second position optical controlling for at least one criterion of single sample 180, e.g., by employing optical control 260. Further in connection with big dissociated sample(s) 180, the method may include removing sample(s) 180 if the at least one criterion is not met.

According to some embodiments of the invention, the number of sample(s) 180 provided to, e.g., carrier(s) 120 at sample-providing station 141 may exceed the number of immobilization sites, thereby obtaining non-immobilizable sample(s). The method may thus include removing non-immobilized sample(s) 180 from carrier(s) 120 at sample-extraction station 151, prior to proceeding to microinjection station 142. In the event that a selected single sample 180 does not meet said at least one criterion; said method may further include mobilizing and removing selected single sample 180.

Embodiments of the present invention enable the microinjection of, for example, at least 2000 samples or cells in 24 hours. The term "hard-to-transfect cells" may refer, for example, to lymphocytes, CTLL2, trypsinized and suspended CaCo2/TC7 cells. Large dissociated cells may refer, for example, to Xenopus Laevis oocytes.

It should be noted that embodiments of the present invention may be operable at temperatures ranging, for example, from 4° C. to 37° C.

It should be noted that each optical control used herein may be performed at a plurality of instances to ensure the validity of the control.

It should be noted that the term "immobilizing", "immobilization", as well as grammatical variations thereof refer to the positional confinement of samples at specific locations in spite of conveyance of the samples to different stations and/or the engagement of the needle with any of the immobilized samples.

It should be noted that the term "conical" as used herein also encompasses the meaning of the term "substantially conical".

The terms "right", "left", "bottom", "below", "lowered", "low", "top", "above", "elevated" and "high" as well as grammatical variations thereof as used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

It should be noted that terms "negative pressure" and "positive pressure" may be relate to pressure values in relation to the surrounding pressure. Therefore, negative pressure may be relative negative pressure and positive pressure may be relative positive pressure.

The invention claimed is:

1. A microinjection apparatus, comprising:
   a microinjection device for microinjection of substances into individual samples by puncturing the samples with an injection needle,
   at least one carrier on which at least one sample is immobilizable,
   wherein the apparatus comprises a drivable support on which the at least one carrier is positionable,
   wherein the drivable support is operative to drive the at least one carrier in a closed loop to a respective plurality of stations that are located at different positions along the loop, and
   a sample supply line, configured to provide at least one sample of a dissociated cell of the type Xenopus Oocyte suspended in a liquid, having a predetermined length that allows each one of the at least one samples of dissociated cells of the type Xenopus Oocyte to be guided by gravity into an orientation suitable for performing microinjection of the dissociated cells of the type Xenopus Oocyte prior to being provided onto the at least one carrier.

2. The microinjection apparatus of claim 1, wherein the apparatus comprises at least one sample-removal station for the removal of at least one sample, the at least one sample-removal station comprising a pressurizing device operative to remove samples from a carrier located at the at least one sample-removal station through suction.

3. The microinjection apparatus of claim 1, wherein the support is embodied by at least one of the following: a turntable, an endless conveyer belt, and a channel.

4. The microinjection apparatus of claim 1, wherein the at least one carrier comprises at least one immobilization site operative to hold a sample by one or more of the following: shape of the carrier, suction and surface chemistry.

5. The microinjection apparatus according to claim 1, wherein the microinjection device is configured to perform microinjection with said injection needle in accordance with at least one of the following: a force-feedback control; a predefined nominal penetration depth; and an optical control.

6. The microinjection apparatus according to claim 1, further comprising an optical control configured to determine a position and/or an orientation of a sample for microinjection.

7. The microinjection apparatus according to claim 1, further comprising an inactive stopover location between a given position and a subsequent position at which a turntable can be stopped whilst simultaneously at least one station at at least one of the following positions is active: at another given position, and at a subsequent respective position.

8. The microinjection apparatus according to claim 1, comprising:
   a drive coupled to the drivable support; and
   a control module controlling the drive and the microinjection device,
   wherein the control module is configured to control the microinjection device and the drive to perform microinjection of at least 2000 samples or cells in 24 hours.

9. An apparatus, comprising:
   a carrier configured to receive a dissociated cell;
   a drivable support, on which the carrier is positioned, operative to drive the carrier in a closed loop to a respective plurality of stations that are located at different positions along the loop; and
   a supply line having a predetermined length and positioned such that a dissociated cell having an animal pole and a vegetal pole within the supply line is oriented, due to gravity, with the animal pole thereof being faced up relative to the carrier, prior to being provided on the carrier,
   wherein a microinjection device comprising an injection needle for microinjection of a substance into the dissociated cell provided on the carrier is one of the stations located at one of the positions along the loop.

* * * * *